United States Patent [19]

Kumagai et al.

[11] Patent Number: 6,146,878
[45] Date of Patent: Nov. 14, 2000

[54] TYROSINE REPRESSOR GENE OF A BACTERIUM BELONGING TO THE GENUS ERWINIA

[75] Inventors: Hidehiko Kumagai, Ohtsu; Hideyuki Suzuki, Kyoto; Takane Katayama, Kasugai, all of Japan

[73] Assignee: Ajinomoto Co., Inc., Tokyo, Japan

[21] Appl. No.: 09/258,349

[22] Filed: Feb. 26, 1999

[30] Foreign Application Priority Data

Feb. 27, 1998 [JP] Japan .................................. 10-048070

[51] Int. Cl.[7] .......................... C07H 21/02; C07H 21/04; C12H 1/00; C12N 1/12; C12N 1/20
[52] U.S. Cl. ..................... 435/252.3; 536/23.4; 536/24.1; 435/243; 435/252.1; 435/252.8; 530/350
[58] Field of Search .................................. 536/23.1, 23.4, 536/24.1; 435/243, 252.1, 252.8; 530/350

[56] References Cited

PUBLICATIONS

Edwina et al. J. Bacteriol 152 = 1276–1279, 1982.
Cornish E. C. J Biol Chem 261 = 403–410, 1986.
Smith HQ J Bacteriolgy 179 (8) = 5914–21, 1997.
Foor Appl Environ Microbiol 59 (9) = 3070–3075, 1993.
Hideyuki Suzuki et al, "Transcriptional Regulation Of Tyrosine Phenol–Lyase Gene Of *Erwinia Herbicola* AJ2985", Biosci. Biotech, Biochem., 59 (12), 2339–2341 (1995).
Paul Singleton Bacteria in Biology, Biotechnology and Medicine pp. 136–140, 1999.

*Primary Examiner*—Phuong T. Bui
*Assistant Examiner*—Li Lee
*Attorney, Agent, or Firm*—Oblon, Spivak, McClelland, Maier & Neustadt, P.C.

[57] ABSTRACT

Using as a host *Escherichia coli* which expresses lactose operon under the control of the promoter/enhancer of tyrosine phenol lyase gene derived from *Erwinia herbicola*, a DNA fragment coding for tyrosine repressor (tyrR) having an amino acid sequence depicted in SEQ ID NO: 2 in Sequence Listing is obtained from the chromosome gene library of *Erwinia herbicola*.

12 Claims, 4 Drawing Sheets

TYROSINE REPRESSOR GENE OF A BACTERIUM BELONGING TO THE GENUS ERWINIA

FIELD OF THE INVENTION

The present invention relates to a tyrosine repressor gene of a bacterium belonging to the genus Erwinia and more particularly to a DNA fragment coding for a tyrosine repressor. The DNA fragment can be used for large scale expression and production of tyrosine phenol lyase (also referred to as "β-tyrosinase") useful for production of L-DOPA or L-tyrosine using recombinant microorganisms.

DESCRIPTION OF THE PRIOR ART

Various amino acids have been produced by direct fermentation by microorganisms. On the other hand, for amino acids which are hard to be produced by direct fermentation, there have been known methods for producing these amino acids (e.g., L-DOPA, L-aspartic acid, L-alanine, L-cysteine, and the like) in which enzymes derived from microorganisms are used.

Among the above-described amino acids, L-DOPA is produced by using tyrosine phenol lyase. This enzyme is known to be produced by a wide variety of microorganisms such as those belonging to the genus Escherichia, Pseudomonas, Flavobacterium, Bacillus, Serratia, Xanthomonas, Agrobacterium, Acromobacter, Aerobacter, Erwinia, Proteus, Salmonella, Citrobacter, Enterobacter, or the like (Japanese Patent No. 2,521,945, and Japanese Patent Publication No. 6-98,003) and its enzymological properties have been elucidated (*Biochem. Biophys. Res. Commun.*, 33, 10 (1963)).

It is suggested that the expression of a tyrosine phenol lyase gene useful for production of L-DOPA is induced by the participation of a tyrosine repressor (TyrR) by the gene derived from *Erwinia herbicola* (H. Suzuki et al., *Biosci. Biotech. Biochem.*, 59, 2339–2341 (1995)). In this report, Suzuki et al. showed the presence of a consensus sequence of a binding site for a tyrosine repressor in a transcription regulatory region of a tyrosine phenol lyase gene and considered that the tyrosine repressor participates in positive control of the transcription of the gene concerned.

On the other hand, Smith et al. introduced a DNA obtained by binding the transcription regulatory region of a tyrosine phenol lyase gene derived from *Citrobacter freundii* to a reporter gene (β-galactosidase gene) into *Escherichia coli* which harbors a tyrosine repressor and *Escherichia coli* which is deficient in a tyrosine repressor and showed that the tyrosine repressor undertakes positive control of the transcription of the tyrosine phenol lyase gene (H. Q. Smith et al., *J. Bacteriol.*, 179, 5914–5921 (1997)).

Also, the tyrosine repressor is known to negatively control the biosynthesis of aromatic amino acids such as tyrosine and the structure of a tyrosine repressor gene of *Escherichia coli* was disclosed (E. C. Cornish et al., J. Biol. Chem., 261, 403–410 (1986)).

However, in microorganisms having a tyrosine phenol lyase gene, particularly in bacteria belonging to the genus Erwinia, which are known to highly express tyrosine phenol lyase, nucleotide sequences of the structural genes and upstream region thereof are known (H. Suzuki et al., *J. Ferment. Bioeng.*, 75, No. 2, 145–148 (1993)) but tyrosine repressor and gene coding therefor have not been clarified yet.

SUMMARY OF THE INVENTION

The present invention has been made in view of the above points and it is an object of the present invention to elucidate the relationship between a tyrosine repressor of bacterium belonging to the genus Erwinia and expression of tyrosine phenol lyase gene and obtain a tyrosine repressor gene for application to L-DOPA production.

With view to solving the above problem, the present inventors have disrupted the tyrosine repressor gene of *Escherichia coli* and introduced into its chromosome a gene fragment comprising a promoter/enhancer region of tyrosine phenol lyase gene (tpl) derived from *Erwinia herbicola* and a lactose operon (lac) ligated downstream thereof. Then, using the resulting strain as a host, the inventors have been successful in obtaining a clone strongly expressing β-galactosidase activity in the presence of tyrosine from the chromosomal gene library of *Erwinia herbicola* and isolating a gene fragment containing tyrosine repressor gene derived from *Erwinia herbicola*, thus completing the present invention.

That is, the present invention provides a DNA fragment coding for tyrosine repressor derived from *Erwinia herbicola* which is defined in the following (A) or (B):

(A) a protein having an amino acid sequence described in SEQ ID NO: 2 in Sequence Listing; or (B) a protein which having an an amino acid sequence including deletion, substitution, insertion or addition of one or several amino acids in the amino acid sequence described in SEQ ID NO: 2 in Sequence Listing, and which has an activity to positively control a expression of tyrosine phenol lyase gene.

In a preferred embodiment, the present invention provides a DNA fragment as defined in the following (a) or (b):

(a) a DNA which contains a nucleotide sequence corresponding to at least nucleotide numbers of 442 to 2004 of the nucleotide sequence depicted in SEQ ID NO: 1 in Sequence Listing, (b) a DNA which is hybridizable under a stringent condition with the nucleotide sequence corresponding to at least nucleotide numbers of 442 to 2004 of the nucleotide sequence depicted in SEQ ID NO: 1 in Sequence Listing, and which codes for a protein having an activity to positively control a expression of tyrosine phenol lyase gene.

In another embodiment, the present invention provides the above-described DNA fragment, wherein the DNA fragment further comprises a DNA sequence consisting a sequence corresponding to nucleotide numbers of 1 to 303 in the nucleotide sequence depicted in SEQ ID NO: 1 in Sequence Listing or a part thereof having a promoter activity, the sequence controlling the expression of a tyrosine repressor.

Further, the present invention provides a recombinant DNA comprising the above-described DNA fragment.

By the present invention, a tyrosine repressor gene of a bacterium belonging to the genus Erwinia is provided. This gene can be utilized for expression regulation of a tyrosine phenol lyase gene and is applicable to the production of L-DOPA.

DETAILED DESCRIPTION OF THE INVENTION

Figure 1:
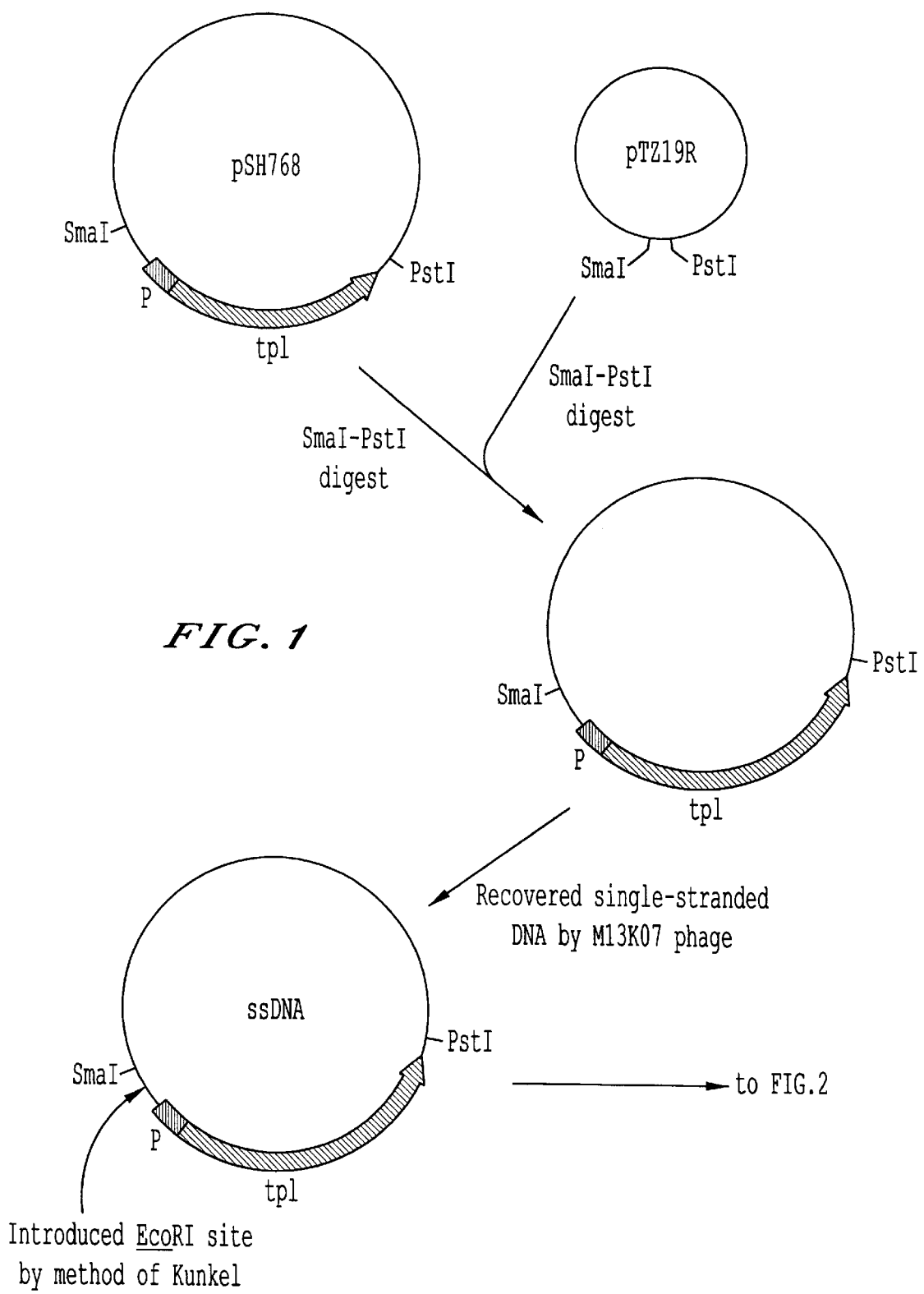
FIG. 1 is a diagram illustrating a part of a process of constructing a plasmid pTK312 harboring a gene coding for tpl'-'lac fused protein.

Hereafter, the present invention will be described in more detail.

The DNA fragment of the present invention can be selected from the chromosome gene library of *Erwinia herbicola* by use of *Escherichia coli* which is deficient in a tyrosine repressor gene and expresses lactose operon under the control of the promoter/enhancer of tyrosine phenol lyase gene derived from *Erwinia herbicola*.

When chromosome DNA fragment of *Erwinia herbicola* containing a tyrosine repressor gene is introduced into the above-described *Escherichia coli*, the expression of lactose operon, which is controlled by the promoter/enhancer of tyrosine phenol lyase gene, is positively controlled by tyrosine repressor expressed by the gene in the DNA fragment, and then β-galactosidase is expressed. The expression of β-galactosidase can be detected, for example, by use of MacConkey-Lactose medium containing L-tyrosine (5 mM) and observation of a colony on the medium turning into red.

The *Escherichia coli* which is deficient in tyrosine repressor gene can be obtained by introducing a tyrosine repressor gene having a mutation showing a phenotype of deletion type (for example, tyrR366 (H. Camakaris et al., J. Bacteriol., 115, 1135–1144 (1973)) by P1 transduction, or the like. Deletion of a tyrosine repressor gene results in 3-fluorotyrosine resistance and, hence, the resistance can be used for confirming deletion of the gene concerned. Also, use of this property as an index in screening mutation treated *Escherichia coli* strains enables one to obtain the *Escherichia coli* which is deficient in a tyrosine repressor gene.

To express lactose operon under the control of the promoter/enhancer of tyrosine phenol lyase gene derived from *Erwinia herbicola*, a DNA obtained by ligating a lactose operon gene to downstream of the promoter/enhancer region may be harbored in an *Escherichia coli* cell.

The promoter/enhancer region of tyrosine phenol lyase gene of *Erwinia herbicola* can be obtained from plasmid pSH768 containing it (H. Suzuki et al., J. Ferment. Biol., 75, 145–148 (1993)). Since their nucleotide sequence has been reported (H. Suzuki et al., J. Ferment. Biol., 75, 145–148 (1993)), tyrosine phenol lyase gene and its upstream region can be obtained from *Erwinia herbicola* chromosomal DNA or chromosome gene library by preparing an oligonucleotide based on the sequence and performing a PCR or hybridization using it.

Incidentally, bacteria which have been hitherto classified into *Erwinia herbicola* are reclassified into *Pantoea agglomerans* at present. Since the Genus Erwinia are closely relative to the genus Pantoea, the DNA of the present invention may be obtained from bacteria belonging to any of genera Erwinia and Pantoea.

The lactose operon and a gene partially deficient in an N-terminal portion of coding region of β-galactosidase gene ('lacZ) in the operon can be obtained by cutting out of pRS552 (R. W. Simons et al., Gene, 53, 85–96 (1987)).

The promoter/enhancer region and lactose operon may be ligated directly. Alternatively, the promoter/enhancer region may be ligated via an N-terminal portion of a coding region of a tyrosine phenol lyase gene (tpl') to a coding region of β-galactosidase gene deleted of an N-terminal portion such that both reading frames can coincide with each other to form a fused gene (tpl'-'lac fused gene), allowing expression of a fused protein consisting of tyrosine phenol lyase and β-galactosidase (tpl'-'lac fused protein).

In order to harbor in *Escherichia coli* lactose operon that expresses under the control of the promoter/enhancer of tyrosine phenol lyase gene of *Erwinia herbicola* as described above (hereafter, also referred to simply as "lactose operon"), for example, *Escherichia coli* may be transformed with a plasmid containing the lactose operon and the gene may be incorporated into chromosome DNA by homologous recombination. Either of the incorporation of lactose operon and the deletion of the tyrosine repressor gene described above may be preceded.

As described above, the *Escherichia coli* which is deficient in a tyrosine repressor gene and which contains lactose operon in chromosomal DNA may be used as a host for screening *Erwinia herbicola* chromosome gene library.

The *Erwinia herbicola* chromosome gene library can be prepared in the same manner as the method used in preparing a usual gene library. For example, according to the method described in Current protocols in molecular biology 2.4.1 (A. M. Frederick et al., Massachusetts General Hospital, Harvard Medical School, John Wiley & Sons, Inc., 1994), chromosomal DNA is extracted from *Erwinia herbicola* and the resulting DNA is digested with an appropriate restriction enzyme and ligated to a suitable vector to prepare a recombinant vector, thus obtaining a chromosome gene library. As the restriction enzyme, usually Sau3AI or the like is used. However, SalI or SspI may be used since the tyrosine repressor gene of *Erwinia herbicola* has been clarified to be contained in SalI-SspI fragment (about 2.4 kb) as demonstrated in the following working examples. Vectors for preparing gene library are exemplified by pUC19, pUC18, pBR322, pHSG299, pHSG399, pHSG398, RSF1010 or the like.

Then, *Escherichia coli* which is deficient in a tyrosine repressor gene and which has lactose operon incorporated in its chromosomal DNA is transformed by the chromosome gene library prepared as described above. If the tyrosine repressor gene was contains in the recombinant vector, β-galactosidase gene is expressed in the transformed cells. The expression of β-galactosidase can be detected by coloring of colonies in red when the transformed cells are grown on a MacConkey-Lactose medium.

Since there is a possibility that β-galactosidase gene derived from *Erwinia herbicola* is be cloned in the strains on which expression of β-galactosidase gene is detected as described above, it is preferred to confirm whether a tyrosine repressor gene has been introduced in a selected candidate strain. This confirmation can be performed, for example, by preparing a strain harboring tpl'-'lac fused protein gene which lacks a regulatory region locating upstream of a promoter of tyrosine phenol lyase gene where regulatory proteins such as tyrosine repressor are considered to bind, and transforming the strain with the recombinant vector recovered from the candidate strain with observing non-expression of β-galactosidase.

The *Escherichia coli* which is deficient in a tyrosine repressor gene (tyrR$^-$) shows 3-fluorotyrosine resistance but the *Escherichia coli* which harbors a tyrosine repressor gene (tyrR$^+$) shows sensitivity to 3-fluorotyrosine. Therefore, this phenotype may be used for confirming that a tyrosine repressor gene is cloned.

SEQ ID No. 1 shows the nucleotide sequence of the DNA fragment (SalI-SspI fragment) containing a tyrosine repressor gene obtained as described above. In this sequence an open reading frame (ORF) is present (nucleotide Nos. 442 to 2004). An amino acid sequence anticipated by the ORF is shown in SEQ ID NO: 2. This amino acid sequence showed about 72% homology with the tyrosine repressor of *Escherichia coli*. The above-described DNA fragment expressed tyrosine repressor in *Escherichia coli* cells so that it is presumed that the portion of nucleotide Nos. 1 to 303 in SEQ ID NO: 1 contains a promoter region.

Since the structure of the tyrosine repressor gene *Erwinia herbicola* has been elucidated by the present invention, tyrosine repressor gene may be obtained by PCR or hybridization using oligonucleotides which are prepared based on the sequence from *Erwinia herbicola* chromosomal DNA or chromosomal gene library.

The DNA of the present invention may code for tyrosine repressor including substitution, deletion, insertion, addition, or inversion of one or several amino acids at one or a plurality of positions, provided that the tyrosine repressor encoded by the DNA maintains the activity to positively control a expression of tyrosine phenol lyase gene. The number of "several" amino acids differs depending on the position or the type of amino acid residues in the three-dimensional structure of the protein. This is because of the following reason. That is, some amino acids such as isoleucine and valine are amino acids having high homology to one another. The difference in such an amino acid does not greatly affect the three-dimensional structure of the protein. Therefore, the protein encoded by the DNA of the present invention may be one which has homology of not less than 30 to 50% preferably 50 to 70% with respect to the entire 521 amino acid residues for constituting tyrosine repressor, and which has the tyrosine repressor activity.

DNA, which codes for the substantially same protein as tyrosine repressor as described above, can be obtained, for example, by modifying the nucleotide sequence, for example, by means of the site-directed mutagenesis method so that one or more amino acid residues at a specified site involve substitution, deletion, insertion, addition, or inversion. DNA modified as described above can be obtained by the conventionally known mutation treatment. The mutation treatment includes a method for treating DNA coding for tyrosine repressor in vitro, for example, with hydroxylamine, and a method for treating a microorganism, for example, a bacterium belonging to the genus Escherichia harboring DNA coding for tyrosine repressor with ultraviolet irradiation or a mutating agent such as N-methyl-N'-nitro-N-nitrosoguanidine (NTG) and nitrous acid usually used for the mutation treatment.

The substitution, deletion, insertion, addition, or inversion of nucleotide as described above also includes mutation (mutant or variant) which naturally occurs, for example, on the basis of the individual difference or the difference in species or genus of the microorganism which harbors tyrosine repressor gene.

The DNA, which codes for substantially the same protein as tyrosine repressor, can be obtained by expressing DNA having mutation as described above in an appropriate cell, and investigating the tyrosine repressor activity of an expressed product. The DNA, which codes for substantially the same protein as tyrosine repressor, can be also obtained, from DNA coding for tyrosine repressor having mutation or from a cell harboring it, by isolating DNA which is hybridizable with DNA having, for example, a nucleotide sequence corresponding to nucleotide numbers of 442 to 2004 of the nucleotide sequence depicted in SEQ ID NO: 1 in Sequence Listing under a stringent condition, and which codes for a protein having the tyrosine repressor activity to positively control a expression of tyrosine phenol lyase gene. The "stringent condition" referred to herein is a condition under which so-called specific hybrid is formed, and non-specific hybrid is not formed. It is difficult to clearly express this condition by using any numerical value. However, for example, the stringent condition includes a condition under which DNA's having high homology, for example, DNA's having homology of not less than 50% are hybridized with each other, and DNA's having homology lower than the above are not hybridized with each other. Alternatively, the stringent condition is exemplified by a condition under which DNA's are hybridized with each other at a salt concentration corresponding to an ordinary condition of washing in Southern hybridization, i.e., 60° C., 1×SSC, 0.1% SDS, preferably 0.1×SSC, 0.1% SDS.

The gene, which is hybridizable under the condition as described above, includes those having a stop codon generated in the middle of the gene, and those having no activity due to mutation of active center. However, such inconveniences can be easily excluded by ligating the gene with a commercially available expression vector, and measuring the tyrosine repressor activity in accordance with the method described above.

The tyrosine repressor gene of the present invention may be utilized for the control of expression of tyrosine phenol lyase gene. For example, transformation of a microorganism with a recombinant DNA obtained by ligating the tyrosine repressor gene of the present invention to a suitable vector will increase the amount of tyrosine phenol lyase expressed. Tyrosine phenol lyase may be utilized in the production of L-DOPA by an enzymatic method.

DESCRIPTION OF THE PREFERRED EMBODIMENT

Hereafter, the present invention will be described more concretely by following Examples.

EXAMPLE 1

<1> Preparation of Chromosome Gene Library of *Erwinia herbicola*

According to the method of Current protocols in molecular biology 2.4.1 (A. M. Frederick et al., Massachusetts General Hospital, Harvard Medical School, John Wiley & Sons, Inc., 1994), chromosomal DNA (1.45 mg) was extracted from *Erwinia herbicola* strain AJ2985 (ATCC21434). The resulting DNA (43.5 µg) was partially digested in a reaction mixture (50 µl) with Sau3AI (6 units) for 10 minutes or 15 minutes and then subjected to agarose electrophoresis to recover about 4 to 8 kb DNA fragment (5.1 µg).

Five µg of pBR322 (Toyobo) was digested with BamHI (10 units) for 2 hours and complete digestion was confirmed by agarose electrophoretic analysis. Then the digestion product was treated with 2 units of alkaline phosphatase (Toyobo) at 37° C. for 1 hour to effect dephosphorylation of 5'-terminal to obtain about 3 µg of BamHI-digested pBR322 DNA.

The pBR322 DNA (1.4 µg) thus prepared and about 4 to 8 kb DNA fragment (1.7 µg) was ligated in a 80 µl reaction mixture at 16° C. for 1 hour using a DNA ligation kit (TAKARA ligation kit Ver. 2 (Takara Shuzo)). Thus the gene library derived from *Erwinia herbicola* was constructed.

<2> Preparation of Host for Screening (*E. coli* TK453)

As a host for screening which is used for selecting a plasmid clone containing a tyrosine repressor gene (tyrR), Escherichia coli was prepared, which was deficient in a tyrosine repressor gene and which harbored a gene expressing lactose operon under the control of the promoter/enhancer of tyrosine phenol lyase gene (tpl) derived from Erwinia herbicola on its chromosome.

The lactose operon was prepared from pRS552 (R. W. Simons et al., Gene, 53, 85–96 (1987)). The pRS552 is a plasmid which harbors an incomplete lactose operon partially deleted of an N-terminal of lacZ in the lac operon. By ligation of a gene fragment comprising N-terminal and an upstream region of a tyrosine phenol lyase gene (tpl) to lacZ in a pRS552 in the same reading frame, a fused gene is constructed, which expresses a fused protein (tpl'-'lac fused protein) consisting of the N-terminal portion of tyrosine phenol lyase (tpl') and the C-terminal portion of β-galactosidase which lacks a part of N-terminal region under the control of tpl. This makes it possible to examine the transcription control of tpl in Escherichia coli by use of β-galactosidase activity as an index.

The promoter/enhancer region of tpl was prepared from a plasmid pSH768 which harbors the region (H. Suzuki et al., J. Ferment. Biol., 75, 145–148 (1993)).

Figure 2:
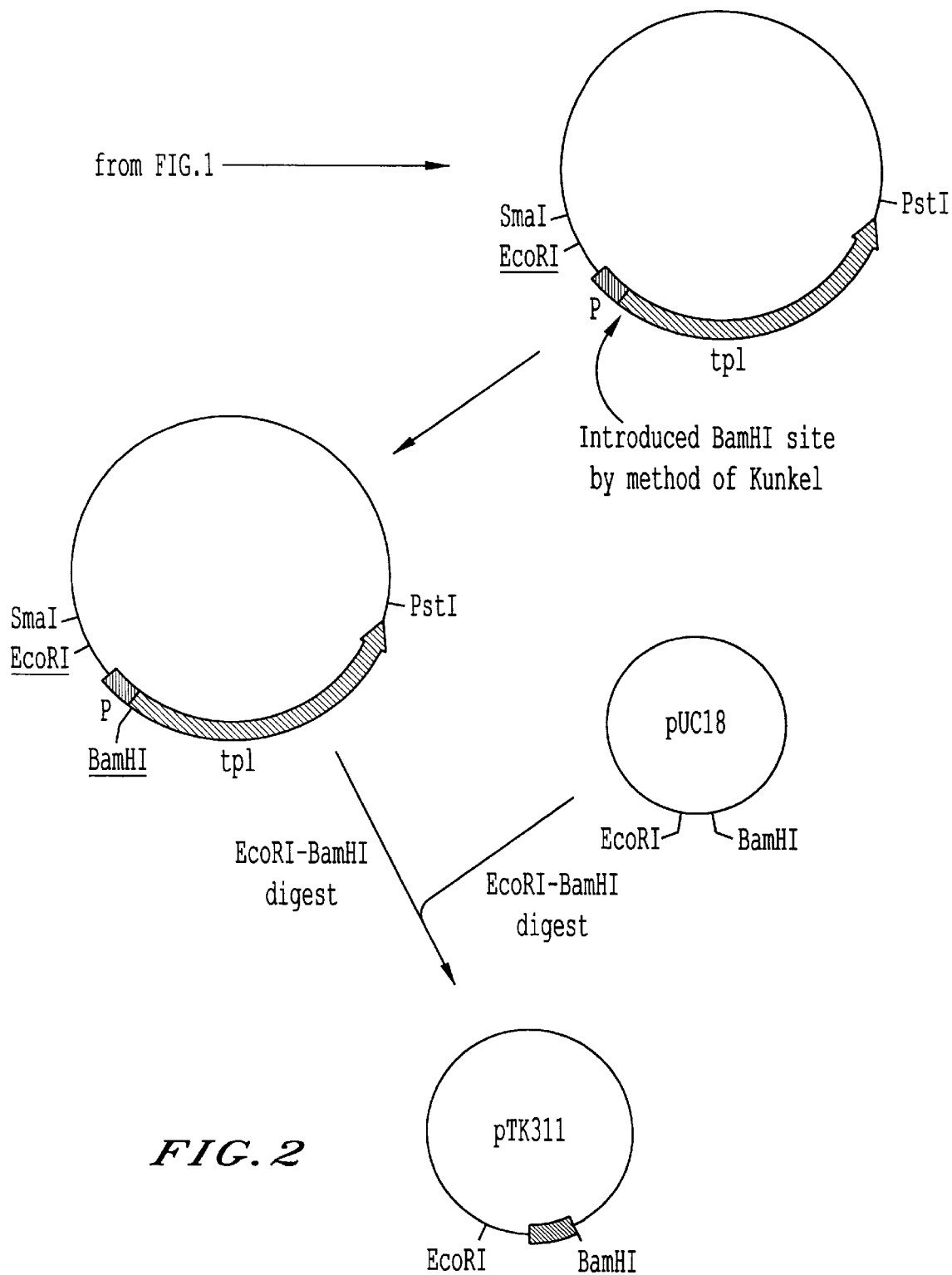
FIG. 2 is a diagram illustrating a part of a process of constructing a plasmid pTK312 harboring a gene coding for tpl'-'lac fused protein.
Figure 3:
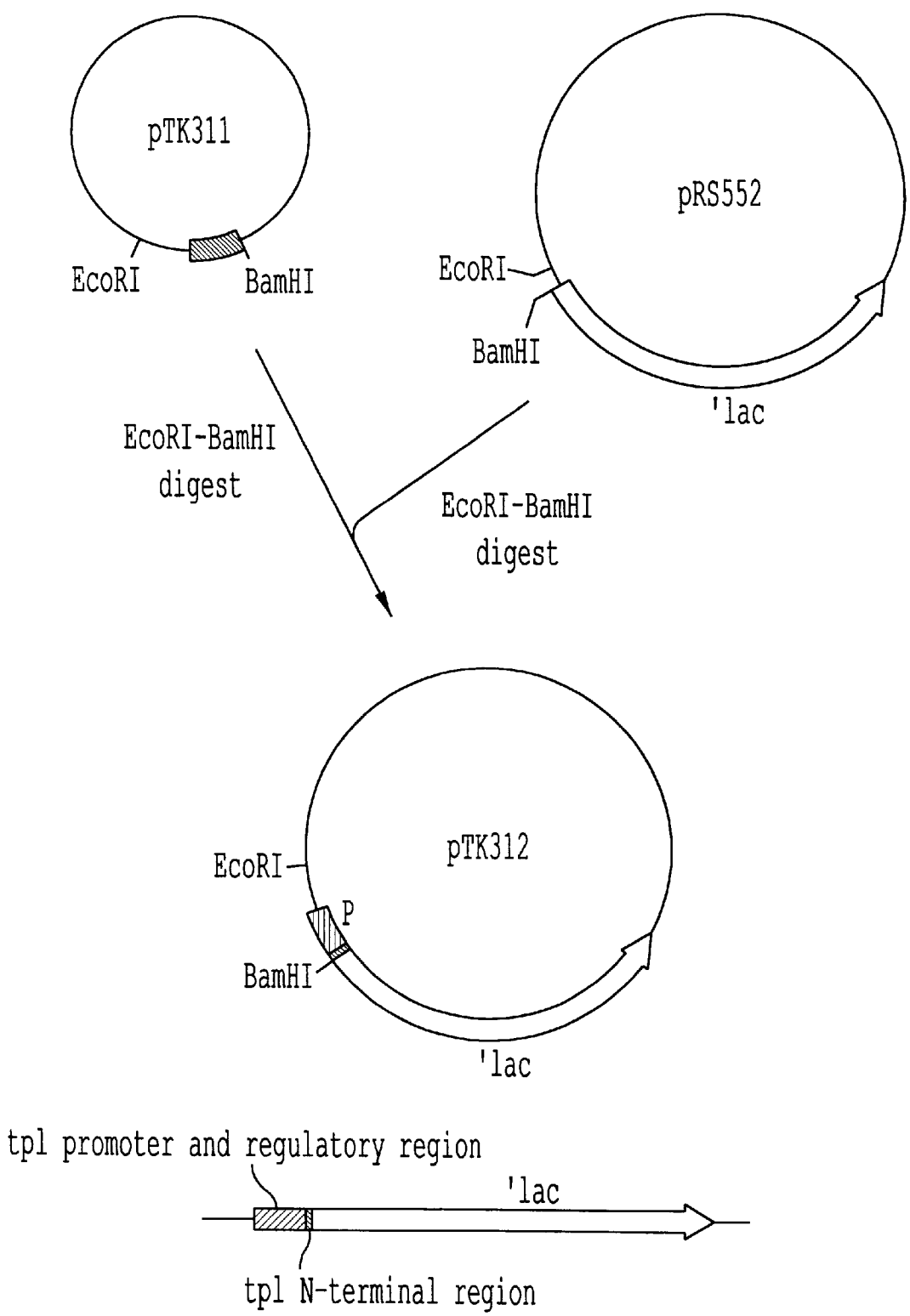
FIG. 3 is a diagram illustrating a part of a process of constructing a plasmid pTK312 harboring a gene coding for tpl'-'lac fused protein.
Figure 4:
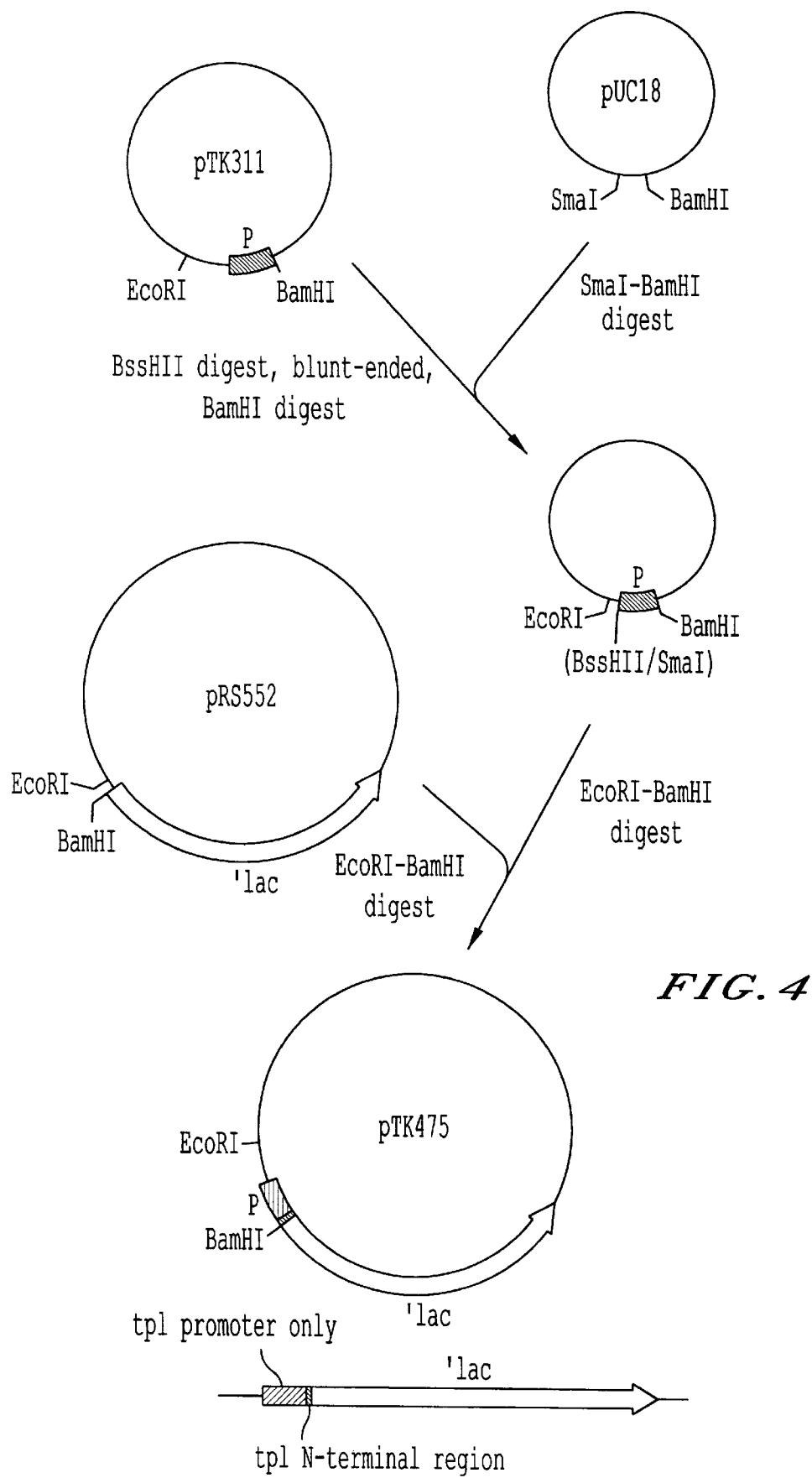
FIG. 4 is a diagram illustrating construction of a plasmid (pTK475) containing a tpl'-'lac fused protein gene deleted of its regulatory region.

First, a plasmid which was used for introducing the above-described gene into Escherichia coli was constructed (FIGS. 1 to 3). The sequence atgaactatcc (SEQ ID NO: 3) corresponding to N-terminus of tpl in pSH768 was converted to atgaaggatcc (SEQ ID NO: 4) in order to BamHI site was introduced, and the sequence ttaacattcgc (SEQ ID NO: 5) which is about 480 bp upstream of the N-terminus was converted to ttagaattcgc (SEQ ID NO: 6) in order to EcoRI site was introduced by site-directed metagenesis. More specifically, this was performed as follows. pSH768 was digested with SmaI and PstI and 2.2 kb fragment of SmaI-PstI was prepared. This fragment was inserted between the SmaI and PstI sites of pTZ19R (Pharmacia) (FIG. 1). Then, the mutations was introduced by site-directed mutagenesis according to the method of Kunkel (Kunkel, T. A., Proc. Natl. Acad. Aci. U.S.A., 82, 488–492 (1985), Kunkel, T. A., Methods in Enzymology, 154, 367–382 (1987)) using Muta-gene phagemid in vitro mutagenesis kit (Bio-Rad)) (FIG. 1 and FIG. 2 supra). The oligonucleotide sequences used for the introduction of BamHI and EcoRI sites were 5'-tcggcaggatccttcatgttta-3' (SEQ ID NO: 7) and 5'-agcggcgaattctaatgacgtg-3' (SEQ ID NO: 8).

Thereafter, about 480 bp gene fragment digested with EcoRI and BamHI was inserted into EcoRI and BamHI site of pUC18 (pTK311), the nucleotide sequence of the inserted fragment portion was determined to confirmed that EcoRI and BamHI were made properly in the targeted positions (FIG. 2). After the confirmation, about 480 bp gene fragments digested with EcoRI and BamHI were inserted into the EcoRI and BamHI site of pRS552 to prepare a plasmid harboring a gene coding for tpl'-'lac fused protein (pTK312) (FIG. 3).

Next, E. coli TE2680 (T. Elliott, J. Bacteriol., 174, 245–253 (1992)) was transformed with the pTK312 harboring tpl'-'lac fused gene. The method for transformation and preparation for competent cells used therein were performed according to H. Inoue and H. Nojima, "Method for Preparing Gene Library", p19–26, 1995 (Yodosha). Since pTK312, which is derived from pRS552, and chromosome of TE2680 have homologous regions (kanamycin resistant gene and lac gene), homologous recombination occurs at certain frequencies and as a result, a strain in which a single copy of a gene coding for tpl'-'lac fused protein was incorporated in its chromosome can be constructed. The strain thus obtained was designated TK314.

The strain TK314 has recD and thereby the strain is deficient in exonuclease activity of exonuclease V, so that linear DNA is free of digestion in cells). In such a strain, plasmids are not replicated stably and therefore it is difficult to use this strain as a host for chromosome gene library of Erwinia herbicola. Accordingly, circumferential genes containing a gene coding for tpl'-'lac fused protein in TK314 was transduced in E. coli JM107 by P1 transduction (A Short Course in Bacterial Genetics, J. H. Miller, Cold Spring Harbor Laboratory Press, Cold Spring Harbor N.Y. 1992).

Since it was suggested that the gene coding for tpl'-'lac fused protein was activated by a tyrosine repressor gene of E. coli (H. Suzuki et al., Bio sci. Biotech. Biochem., 59, 2339–2341 (1995), H. Q. Smith et al., J. Bacteriol., 179, 5914–5921 (1997)), tyrR366 (H. Camakaris et al., J. Bacteriol., 115, 1135–1144 (1973)) was introduced by P1 transduction in order to inactivate the function of chromosomal tyrR of E. coli JM107. And lastly, in order to convert the transductant to recA⁻, Δ(srl-recA)306::Tn10 was introduced from MV1184 (Methods in Enzymology, 153, 3–11 (1987)) and the resulting strain was named TK453. Competent cells were prepared using TK453 and used as a host for screening chromosome gene library Erwinia herbicola.

<3> Screening of a Clone Activating Expression of tpl'-'lac Fused Protein Gene Form Chromosome Gene Library After transforming TK453 with the library (8 μl) prepared as described above, the transformed cells were plated on a MacConkey-Lactose (Difco) medium containing 5 mM L-tyrosine and about 20,000 colonies were obtained. Among them, 23 colonies showed the phenotype of red colour, which is an index for expression of β-galactosidase gene (lacZ). This phenotype would suggest that the chromosome DNA fragment inserted in the plasmids introduced in the colonies contains the targeted tyrR or β-galactosidase gene. Alternatively, there is the possibility that other unknown gene(s) may be contained.

Accordingly, for further confirmation, a strain (TK481) having tpl'-'lac fused protein gene, which is removed of a regulatory region upstream of tpl promoter where regulatory proteins such as tyrR are considered to bind was prepared. That is, after treating plasmid pTK311 with BssHIII, the termini were blunt-ended. Then the plasmid was digested with BamHI to cut out a BssHIII-BamHI 180 bp fragment. This fragment was inserted in the SmaI and BamHI sites of pUC18, and the resulting plasmid was digested with EcoRI and BamHI to obtain an about 190 bp fragment. This fragment and pRS552 which was digested with EcoRI and BamHI were ligated to each other and resulting plasmid pTK475 was obtained (FIG. 2). Then, E. coli TE2680 was transformed with pTK475 and chromosomal homologous recombination was performed in the same manner as described above to obtain TK481.

Since TK481 was removed of upstream regulatory region of tpl, no protein that participates in the expression regulation of tpl can act thereon, resulting in that tpl'-'lac fused protein gene does not express substantially. Hence, TK481 was transformed by a plasmid which was prepared from the strain that showed phenotype of red colour in the primary screening. Then strains showing phenotype of white colour were selected from transformants. The secondary screening gave 20 strains. In all the plasmids of these strains, about 1.6 kb DNA fragments were detected upon EcoRI digenstion. All of the cells of the transformants showed sensitivity to 3-fluorotyrosine (in E. coli, tyrR⁺ is 3-fluorotyrosine resistant; H. Camakaris et al., J. Bacteriol., 115, 1135–1144 (1973)), showing the same properties as tyrR⁺ phenotype in E. coli. These results strongly suggested that these clones have a DNA fragment containing a certain identical DNA region which contains tyrR of *Erwinia herbicola*.

Among the above-described candidate strains, a plasmid having tyrR was named pTK-#20 and used in the subsequent operations. In order to make the DNA fragment having tyrR shorter, about 2 kb or more gene fragments obtained by digestion with various restriction enzymes (EcoRI, BssHII, EcoRV, HpaI, SalI, SphI, NruI, and the like) were subcloned in pBR322, TK453 was transformed with the resulting plasmids, and those colonies turned red on a MacConkey-Lactose (Difco) medium containing 5 mM L-tyrosine were selected in the same manner as described above. As a result, as DNA fragment harbored in the selected strains, 3.5 kb fragments were obtained after digestion with SalI and SphI, respectively. Of these, the 3.5 kb of SalI fragment was transferred to pUC18 and the nucleotide sequence of the fragment was determined using a DNA sequencer (Shimadzu DSQ~1000L) (SEQ ID NO: 1). This DNA fragment contains an open reading frame (nucleotide Nos. 442 to 2004), and an amino acid sequence deduced from the ORF (SEQ ID NO: 2) had a homology of about 72% with TyrR of *E. coli*.

EXAMPLE 2

Expression and Comparison of Functions of tyrR of *E. coli* and tyrR of *Erwinia herbicola* in *E. coli*

Comparison of the functions of tyrR of *E. coli* and tyrR of *Erwinia herbicola* with respect to promoter/enhancer of tpl were examined by comparing β-galactosidase expression.

Expression plasmid of tyrR of *E. coli* was constructed as follows. From a plasmid pMU400 containing tyrR of *E. coli* (C. Edwina et al., J. Bacteriol., 152, 1276–1279 (1982))and tyrR of *Erwinia herbicola* was digested by NdeI and HindIII to obtain an about 2.6 kb fragment. After the termini were blunt-ended with T4 DNA polymerase, it was inserted in EcoRV site of pBR322 (Toyobo) to prepare pTK559. In a similar manner, expression plasmid of tyrR of *Erwinia herbicola* was constructed. Namely, an about 2.4 kb fragment obtained by digesting pTK-#20 prepared in Example 1 with SspI and SalI was blunt-ended and inserted in EcoRV site of pBR322 to prepare pTK561.

The pTK559 and pTK561 were used to transform competent cell TK453 prepared in <2> of Example 1 to obtain TK564 and TK565, respectively. Using the both strains, expression of β-galactosidase was examined.

TK564 and TK565 were inoculated in large test tubes which contain 10 ml of M9 Medium (A short Course in Bacterial Genetics, J. H. Miller, Cold Spring Harbor Laboratory Press, Cold Spring Harbor N.Y. 1992) containing 2 g/L glycerol, 1 mM thiamine, 0.1 mM L-tryptophan, 30 μ/ml kanamycin, 15 μg/L tetracycline, 100 μg/L ampicillin or the same medium further containing 2 mM L-tyrosine (10 ml) and cultivated at 37° C. to an optical density at 600 nm ($OD_{600}$) of about 0.6 to about 0.9, followed by measurement of β-galactosidase activity (Miller units) by the method of J. H. Miller et al. (A Short Course in Bacterial Genetics, 71–80, Cold Spring Harbor laboratory, Cold Spring Harbor, N.Y. (1992)). As a result, as shown in Table 1, TK564 and TK565 showed about 10 to 20 fold increase in β-galactosidase activity by addition of 2 mM L-tyrosine. As compared with TK564 having tyrR of *E. coli*, TK565 having tyrR of *Erwinia herbicola* exhibited about 2 fold induction effect.

TABLE 1

| Strain | β-Galactosidase Activity | |
|---|---|---|
| | M9 Medium | M9 Medium (L-tyrosine added) |
| TK564 | 29.1 | 324 |
| TK565 | 35.5 | 656 |

The results above confirmed that the SalI-SspI 2.4 kb fragment obtained as described above contained tyrR of *Erwinia herbicola*.

What is claimed is:

1. A purified DNA fragment coding for a tyrosine repressor of *Erwinia herbicola*, comprising an amino acid sequence described in SEQ ID NO:2.

2. A recombinant DNA comprising the DNA fragment as claimed in claim 1.

3. The purified DNA fragment of claim 1, which comprises nucleotides 442–2004 of SEQ ID NO:1.

4. The purified DNA fragment of claim 3, further comprising nucleotides 1–303 of SEQ ID NO:1.

5. The purified DNA fragment of claim 4, wherein nucleotides 1–303 of SEQ ID NO:1 controls the expression of the DNA fragment coding region.

6. The purified DNA fragment of claim 5, wherein the DNA fragment coding region is nucleotides 442–2004 of SEQ ID NO:1.

7. A purified *Erwinia herbicola* DNA fragment that hybridizes under stringent conditions to the purified DNA fragment of claim 3 and codes for a protein having tyrosine repressor activity, wherein the stringent conditions comprise washing at 60° C. in 1×SSC and 0.1% SDS.

8. A vector, comprising the purified DNA fragment of claim 3.

9. A vector, comprising the purified DNA fragment of claim 4.

10. A microorganism, comprising the recombinant DNA of claim 2.

11. A microorganism, comprising the vector of claim 8.

12. A microorganism, comprising the vector of claim 9.

* * * * *

SEQUENCE LISTING

<160> NUMBER OF SEQ ID NOS: 8

<210> SEQ ID NO 1
<211> LENGTH: 3363
<212> TYPE: DNA
<213> ORGANISM: Erwinia herbicola
<220> FEATURE:
<221> NAME/KEY: CDS
<222> LOCATION: (442)..(2004)

<400> SEQUENCE: 1

```
gtcgacgcgt gccgcagggc attggtgcgg ggctgctcac cgcccggctg ggtatcaaag      60
cgatggagct gtgtcggcct ttaccctggc tggaaaatga taaacctcgt ctcggcgatt     120
accgcgggag ctgttagggc agttgaaaga cgcgctacaa aagggcggga ataaacatcc     180
acaaaactga ctttagatgg ggccgttatt taacgtcccc tgtttagcgc gccaaatctg     240
cgggggaccg ttccgggata ctgggaagat taactgcgaa agacgtcgaa aactcaaggt     300
gttatggcgc gctgcgcgcg acggacgttt aaaaaaaacg cgcttgcgtt aacgctgtca     360
acttttcctg acagccccct ttctgcggac gggctgttta gcgtattatc gcgacatatc     420
```

-continued

```
aaacggatta aggcccacgc a atg cgt tta gaa gtg ttt tgt cag gac cgt      471
             Met Arg Leu Glu Val Phe Cys Gln Asp Arg
              1               5                  10 atc gga ctg gcg cgt gaa ttg ctc gac ctg ttg gtg gcg cgt agt atc     519
Ile Gly Leu Ala Arg Glu Leu Leu Asp Leu Leu Val Ala Arg Ser Ile
             15                  20                  25 gat ctc cgc ggc att gaa gtc gcc gcc tca ggc cgt atc tat ctt aat     567
Asp Leu Arg Gly Ile Glu Val Ala Ala Ser Gly Arg Ile Tyr Leu Asn
         30                  35                  40 ttc tcc acg ctt gaa ttc gaa cag ttc agt aat ctg atg gcg gaa atc     615
Phe Ser Thr Leu Glu Phe Glu Gln Phe Ser Asn Leu Met Ala Glu Ile
             45                  50                  55 cgt cgt aca ccc ggc gtc acc gat gtc cgc acg gtc ccc tat atg ccg     663
Arg Arg Thr Pro Gly Val Thr Asp Val Arg Thr Val Pro Tyr Met Pro
         60                  65                  70 tct gaa cgt gaa cat cgg gta ctc agc gcc ttg ctg gtt gcc atg cca     711
Ser Glu Arg Glu His Arg Val Leu Ser Ala Leu Leu Val Ala Met Pro
 75                  80                  85                  90 gag ccg gta ttt tcg gtt gat ttg aga acg aag gtt gag ctg gcg aac     759
Glu Pro Val Phe Ser Val Asp Leu Arg Thr Lys Val Glu Leu Ala Asn
                 95                 100                 105 ccg gcg gcg caa aac ctg ttt aat ctt gat gaa aac aag atc cgc aat     807
Pro Ala Ala Gln Asn Leu Phe Asn Leu Asp Glu Asn Lys Ile Arg Asn
            110                 115                 120 ttt acc gcc gac cac ctg att aac ggt ttt aat ttt gcg cgc tgg ctg     855
Phe Thr Ala Asp His Leu Ile Asn Gly Phe Asn Phe Ala Arg Trp Leu
            125                 130                 135 gag agc gaa cgc gtt cag gcg cag gcg caa cat gtg gtg ata gaa ggg     903
Glu Ser Glu Arg Val Gln Ala Gln Ala Gln His Val Val Ile Glu Gly
140                 145                 150 cgc gac ttc ctg atg gaa gca cac ccg att tac ctg tca gag gac aac     951
Arg Asp Phe Leu Met Glu Ala His Pro Ile Tyr Leu Ser Glu Asp Asn
155                 160                 165                 170 gac cag gcc gac cag ctc gtc ggc gca atg gtg atg ctg aag tct act     999
Asp Gln Ala Asp Gln Leu Val Gly Ala Met Val Met Leu Lys Ser Thr
                175                 180                 185 gcc cgt atg ggg cga caa ctg cag aac ctg gtg gtg acc gat gaa acc    1047
Ala Arg Met Gly Arg Gln Leu Gln Asn Leu Val Val Thr Asp Glu Thr
            190                 195                 200 gag ttc gat cat att gtc gcc gtt acg ccc agg atg cgg cag gtc gtg    1095
Glu Phe Asp His Ile Val Ala Val Thr Pro Arg Met Arg Gln Val Val
            205                 210                 215 gaa cag gcg cgc aag ctc gcg atg cac gat gca ccg ctg ctg att atc    1143
Glu Gln Ala Arg Lys Leu Ala Met His Asp Ala Pro Leu Leu Ile Ile
220                 225                 230 ggc gac acc ggc acg ggc aaa gac atg ctg gcg cgg gcc tgt cat tta    1191
Gly Asp Thr Gly Thr Gly Lys Asp Met Leu Ala Arg Ala Cys His Leu
235                 240                 245                 250 cgc agc gca cgc gga aag atg cct ttt ctg gcg ctt aac tgt gca tcg    1239
Arg Ser Ala Arg Gly Lys Met Pro Phe Leu Ala Leu Asn Cys Ala Ser
                255                 260                 265 ctg ccg gat gac gta gcg gaa agt gag ctt ttt ggt cac gca gcc ggg    1287
Leu Pro Asp Asp Val Ala Glu Ser Glu Leu Phe Gly His Ala Ala Gly
            270                 275                 280 gcc tat ccc aat gcg ctg gag ggc aaa aaa ggc ttt ttc gaa cag gca    1335
Ala Tyr Pro Asn Ala Leu Glu Gly Lys Lys Gly Phe Phe Glu Gln Ala
            285                 290                 295 aac ggt ggc tcg gtg ctg ctg gat gaa att ggc gag atg tca ccc act    1383
Asn Gly Gly Ser Val Leu Leu Asp Glu Ile Gly Glu Met Ser Pro Thr
```

-continued

|  |  |  |  |  |  |  |  |  |  |  |  |  |  |  |  |
|---|---|---|---|---|---|---|---|---|---|---|---|---|---|---|---|
|  | 300 |  |  |  | 305 |  |  |  |  | 310 |  |  |  |  |  |
| atg | cag | acg | aag | ctg | ctg | cgt | ttt | ctg | aac | gat | ggc | act | ttc | cgc | cgc | 1431 |
| Met | Gln | Thr | Lys | Leu | Leu | Arg | Phe | Leu | Asn | Asp | Gly | Thr | Phe | Arg | Arg |  |
| 315 |  |  |  |  | 320 |  |  |  |  | 325 |  |  |  |  | 330 |  |

| gtc | ggt | gag | gag | cat | gag | gta | cac | gtg | aat | gtc | cgc | gtg | atc | tgc | gcc | 1479 |
| Val | Gly | Glu | Glu | His | Glu | Val | His | Val | Asn | Val | Arg | Val | Ile | Cys | Ala |  |
|  |  |  |  |  | 335 |  |  |  |  | 340 |  |  |  |  | 345 |  |

| acc | cag | aag | aac | ctg | ttt | gag | ctg | gtt | cag | cgc | ggc | gag | ttc | agg | gaa | 1527 |
| Thr | Gln | Lys | Asn | Leu | Phe | Glu | Leu | Val | Gln | Arg | Gly | Glu | Phe | Arg | Glu |  |
|  |  |  | 350 |  |  |  |  | 355 |  |  |  |  | 360 |  |  |  |

| gac | ctt | ttc | tat | cgc | ctg | aat | gtg | ctt | acg | ctg | aat | ctg | ccg | ccg | ctg | 1575 |
| Asp | Leu | Phe | Tyr | Arg | Leu | Asn | Val | Leu | Thr | Leu | Asn | Leu | Pro | Pro | Leu |  |
|  |  | 365 |  |  |  |  | 370 |  |  |  |  | 375 |  |  |  |  |

| cgc | gag | cgc | gtt | cag | gac | att | atg | ccg | ctg | acg | gaa | att | ttc | gtg | gcg | 1623 |
| Arg | Glu | Arg | Val | Gln | Asp | Ile | Met | Pro | Leu | Thr | Glu | Ile | Phe | Val | Ala |  |
|  | 380 |  |  |  |  | 385 |  |  |  |  | 390 |  |  |  |  |  |

| cgt | ttc | gcc | gat | gaa | cag | ggc | att | cct | cgg | ccg | cgt | ctt | tcc | tca | cag | 1671 |
| Arg | Phe | Ala | Asp | Glu | Gln | Gly | Ile | Pro | Arg | Pro | Arg | Leu | Ser | Ser | Gln |  |
| 395 |  |  |  |  | 400 |  |  |  |  | 405 |  |  |  |  | 410 |  |

| ctg | aat | gct | ttt | ctg | atg | cgc | tat | aac | tgg | ccc | gga | aac | gtg | cgg | cag | 1719 |
| Leu | Asn | Ala | Phe | Leu | Met | Arg | Tyr | Asn | Trp | Pro | Gly | Asn | Val | Arg | Gln |  |
|  |  |  | 415 |  |  |  |  | 420 |  |  |  |  | 425 |  |  |  |

| ctt | aaa | aat | gcc | ttg | tat | cgt | gca | tta | acc | cag | ttg | gaa | ggc | cat | gag | 1767 |
| Leu | Lys | Asn | Ala | Leu | Tyr | Arg | Ala | Leu | Thr | Gln | Leu | Glu | Gly | His | Glu |  |
|  |  | 430 |  |  |  |  | 435 |  |  |  |  | 440 |  |  |  |  |

| tta | cgg | ccg | cag | gat | atc | gtc | ttg | ccg | gaa | cag | gcg | ctg | gat | gtg | tca | 1815 |
| Leu | Arg | Pro | Gln | Asp | Ile | Val | Leu | Pro | Glu | Gln | Ala | Leu | Asp | Val | Ser |  |
|  |  | 445 |  |  |  |  | 450 |  |  |  |  | 455 |  |  |  |  |

| ctg | ggg | gaa | gaa | gcg | atg | gaa | ggc | acg | ctg | gat | cag | atc | acc | agc | cgc | 1863 |
| Leu | Gly | Glu | Glu | Ala | Met | Glu | Gly | Thr | Leu | Asp | Gln | Ile | Thr | Ser | Arg |  |
|  | 460 |  |  |  |  | 465 |  |  |  |  | 470 |  |  |  |  |  |

| ttt | gaa | cga | tct | att | ttg | acg | cgg | tta | tat | ttg | tct | tat | ccg | agc | acg | 1911 |
| Phe | Glu | Arg | Ser | Ile | Leu | Thr | Arg | Leu | Tyr | Leu | Ser | Tyr | Pro | Ser | Thr |  |
| 475 |  |  |  |  | 480 |  |  |  |  | 485 |  |  |  |  | 490 |  |

| cgc | aaa | ctg | gca | aaa | cga | ctg | ggg | gtt | tcc | cat | acc | gcc | att | gcc | aat | 1959 |
| Arg | Lys | Leu | Ala | Lys | Arg | Leu | Gly | Val | Ser | His | Thr | Ala | Ile | Ala | Asn |  |
|  |  |  |  | 495 |  |  |  |  | 500 |  |  |  |  | 505 |  |  |

| aaa | ctg | cgt | gag | tac | ggt | ctg | ggg | cag | aag | cgc | ggc | gac | aac | gaa |  | 2004 |
| Lys | Leu | Arg | Glu | Tyr | Gly | Leu | Gly | Gln | Lys | Arg | Gly | Asp | Asn | Glu |  |  |
|  |  |  | 510 |  |  |  |  | 515 |  |  |  |  | 520 |  |  |  |

| taaaacgcag cggataagtc tggcttatcc gctgtggcca ttatttcagc gcagcgagtg | 2064 |
| cggcatcata atcgggttca gtggtgatct cattcaccag ctggctgtaa agcactttgt | 2124 |
| catgctcatc cagtacgata acggcacggg ccgtcagacc ctgaagggca ccatcagcaa | 2184 |
| tttccacgcc aaaatctttt ttgaattccc cgccgcgcag cgttgacagc gtaaccacgt | 2244 |
| tgttgaggtt gtctgcgcca caaaaacgcg attgagcaaa gggcaggtcg gcggaaatac | 2304 |
| ataacaccac cgtgttattc agttcgcccg ctaactggtt aaacttgcgc accgaagagg | 2364 |
| cgcacacgcc ggtatcgacg ctgggaaaaa tattcagaat cttgcgtttt cctgcatact | 2424 |
| cagagagtga aacgttagac aggttttttcg ccacgagggt aaaagcgtta acgctatcgc | 2484 |
| ccggctgcgg gaactgacct gcaaccgcta cagggttgcc ctgaaagtga acagtctgag | 2544 |
| acataagaat tccttctaat gatgttatct gacagaaaag aaagcgtcag tacaggtata | 2604 |
| gccattgttt atgacataaa ttttaagggt ttacgagagc atttgttgcc taaagttaaa | 2664 |
| tggcgatgat gaatcccaga gaaaaggaga ggtaatgaga acgtaaaat gttatcccga | 2724 |
| agcatggccg ctgcatacgc cgtttgtcat tgctcgtggc agtcgcaccg aagccaaggt | 2784 |

-continued

```
cgttgtcgtc gaaatcgaag aagagggcgt gaaagggatc ggcgaggcca cgccttacac    2844
gcgctacggc gaaagcgaag ccctggtgct ggaacaaatt gcgaccgtta tgcctcaact    2904
gcagcaaggg ctgtcgcgtg aagccttgca gagcctgttg cctgccggtg cggcaagaaa    2964
cgccatcgac agtgctctct gggaccttgc cgctcgccag cagcatgtga cgctggagca    3024
gttagtgggc gcggaaccga cccagtctgt tgtgactgca cacacggtga gcattgatac    3084
gccggaagcg atggccagca gcgcgcaggc gttgtggcaa catggcgcaa cactgctcaa    3144
aatcaaaatg gacaataact ttattaccga gcgcctgatg gcgattcgcg ctgctgttcc    3204
cgacgcgaca ttacttgtgg atgcgaatga atcctggcat gccgaaggct ggcagcccgt    3264
tgccagctgt tagccgatct ggaggtggcc atgctggaac agccgttacc ggcaggtgaa    3324
gacgcggcgc tggcgaactt tatccatcct cttccgatc                          3363
```

<210> SEQ ID NO 2
<211> LENGTH: 521
<212> TYPE: PRT
<213> ORGANISM: Erwinia herbicola

<400> SEQUENCE: 2

```
Met Arg Leu Glu Val Phe Cys Gln Asp Arg Ile Gly Leu Ala Arg Glu
 1               5                  10                  15

Leu Leu Asp Leu Leu Val Ala Arg Ser Ile Asp Leu Arg Gly Ile Glu
                20                  25                  30

Val Ala Ala Ser Gly Arg Ile Tyr Leu Asn Phe Ser Thr Leu Glu Phe
            35                  40                  45

Glu Gln Phe Ser Asn Leu Met Ala Glu Ile Arg Arg Thr Pro Gly Val
        50                  55                  60

Thr Asp Val Arg Thr Val Pro Tyr Met Pro Ser Glu Arg Glu His Arg
 65                  70                  75                  80

Val Leu Ser Ala Leu Leu Val Ala Met Pro Glu Pro Val Phe Ser Val
                85                  90                  95

Asp Leu Arg Thr Lys Val Glu Leu Ala Asn Pro Ala Ala Gln Asn Leu
            100                 105                 110

Phe Asn Leu Asp Glu Asn Lys Ile Arg Asn Phe Thr Ala Asp His Leu
        115                 120                 125

Ile Asn Gly Phe Asn Phe Ala Arg Trp Leu Glu Ser Glu Arg Val Gln
130                 135                 140

Ala Gln Ala Gln His Val Val Ile Glu Gly Arg Asp Phe Leu Met Glu
145                 150                 155                 160

Ala His Pro Ile Tyr Leu Ser Glu Asp Asn Asp Gln Ala Asp Gln Leu
                165                 170                 175

Val Gly Ala Met Val Met Leu Lys Ser Thr Ala Arg Met Gly Arg Gln
            180                 185                 190

Leu Gln Asn Leu Val Val Thr Asp Glu Thr Glu Phe Asp His Ile Val
        195                 200                 205

Ala Val Thr Pro Arg Met Arg Gln Val Val Glu Gln Ala Arg Lys Leu
    210                 215                 220

Ala Met His Asp Ala Pro Leu Leu Ile Ile Gly Asp Thr Gly Thr Gly
225                 230                 235                 240

Lys Asp Met Leu Ala Arg Ala Cys His Leu Arg Ser Ala Arg Gly Lys
                245                 250                 255

Met Pro Phe Leu Ala Leu Asn Cys Ala Ser Leu Pro Asp Asp Val Ala
            260                 265                 270
```

```
Glu Ser Glu Leu Phe Gly His Ala Ala Gly Ala Tyr Pro Asn Ala Leu
        275                 280                 285

Glu Gly Lys Lys Gly Phe Phe Glu Gln Ala Asn Gly Gly Ser Val Leu
        290                 295                 300

Leu Asp Glu Ile Gly Glu Met Ser Pro Thr Met Gln Thr Lys Leu Leu
305                 310                 315                 320

Arg Phe Leu Asn Asp Gly Thr Phe Arg Arg Val Gly Glu His Glu
                325                 330                 335

Val His Val Asn Val Arg Val Ile Cys Ala Thr Gln Lys Asn Leu Phe
                340                 345                 350

Glu Leu Val Gln Arg Gly Glu Phe Arg Glu Asp Leu Phe Tyr Arg Leu
        355                 360                 365

Asn Val Leu Thr Leu Asn Leu Pro Pro Leu Arg Glu Arg Val Gln Asp
370                 375                 380

Ile Met Pro Leu Thr Glu Ile Phe Val Ala Arg Phe Ala Asp Glu Gln
385                 390                 395                 400

Gly Ile Pro Arg Pro Arg Leu Ser Ser Gln Leu Asn Ala Phe Leu Met
                405                 410                 415

Arg Tyr Asn Trp Pro Gly Asn Val Arg Gln Leu Lys Asn Ala Leu Tyr
                420                 425                 430

Arg Ala Leu Thr Gln Leu Glu Gly His Glu Leu Arg Pro Gln Asp Ile
        435                 440                 445

Val Leu Pro Glu Gln Ala Leu Asp Val Ser Leu Gly Glu Glu Ala Met
        450                 455                 460

Glu Gly Thr Leu Asp Gln Ile Thr Ser Arg Phe Glu Arg Ser Ile Leu
465                 470                 475                 480

Thr Arg Leu Tyr Leu Ser Tyr Pro Ser Thr Arg Lys Leu Ala Lys Arg
                485                 490                 495

Leu Gly Val Ser His Thr Ala Ile Ala Asn Lys Leu Arg Glu Tyr Gly
                500                 505                 510

Leu Gly Gln Lys Arg Gly Asp Asn Glu
        515                 520

<210> SEQ ID NO 3
<211> LENGTH: 11
<212> TYPE: DNA
<213> ORGANISM: Erwinia herbicola

<400> SEQUENCE: 3
atgaactatc c                                                          11

<210> SEQ ID NO 4
<211> LENGTH: 11
<212> TYPE: DNA
<213> ORGANISM: Erwinia herbicola

<400> SEQUENCE: 4
atggaggatc c                                                          11

<210> SEQ ID NO 5
<211> LENGTH: 11
<212> TYPE: DNA
<213> ORGANISM: Erwinia herbicola

<400> SEQUENCE: 5
ttaacattcg c                                                          11
```

-continued

```
<210> SEQ ID NO 6
<211> LENGTH: 11
<212> TYPE: DNA
<213> ORGANISM: Erwinia herbicola

<400> SEQUENCE: 6
ttagaattcg c                                                           11

<210> SEQ ID NO 7
<211> LENGTH: 22
<212> TYPE: DNA
<213> ORGANISM: Erwinia herbicola

<400> SEQUENCE: 7
tcggcaggat ccttcatgtt ta                                               22

<210> SEQ ID NO 8
<211> LENGTH: 22
<212> TYPE: DNA
<213> ORGANISM: Erwinia herbicola

<400> SEQUENCE: 8
agcggcgaat tctaatgacg tg                                               22
```